US010159537B2

(12) United States Patent
Cheng

(10) Patent No.: US 10,159,537 B2
(45) Date of Patent: Dec. 25, 2018

(54) HUMAN TISSUE RADIATION PROTECTOR WITH AUXILIARY METHOD OF RADIOTHERAPY

(71) Applicant: Hsiao-Hsu Cheng, Taipei (TW)

(72) Inventor: Hsiao-Hsu Cheng, Taipei (TW)

( * ) Notice: Subject to any disclaimer, the term of this patent is extended or adjusted under 35 U.S.C. 154(b) by 0 days.

(21) Appl. No.: 15/232,281

(22) Filed: Aug. 9, 2016

(65) Prior Publication Data

US 2016/0361130 A1 Dec. 15, 2016

Related U.S. Application Data

(63) Continuation of application No. 14/249,766, filed on Apr. 10, 2014, now abandoned.

(51) Int. Cl.
| | |
|---|---|
| *A61N 5/10* | (2006.01) |
| *A61B 90/00* | (2016.01) |
| *A61L 31/02* | (2006.01) |
| *A61L 31/14* | (2006.01) |
| *A61L 31/18* | (2006.01) |
| *A61M 29/02* | (2006.01) |
| *A61M 25/10* | (2013.01) |

(52) U.S. Cl.
CPC .............. *A61B 90/04* (2016.02); *A61B 90/02* (2016.02); *A61L 31/028* (2013.01); *A61L 31/14* (2013.01); *A61L 31/18* (2013.01); *A61M 29/02* (2013.01); *A61N 5/10* (2013.01); *A61N 5/1071* (2013.01); *A61B 2090/0427* (2016.02); *A61B 2090/0445* (2016.02); *A61B 2090/0481* (2016.02); *A61M 2025/1079* (2013.01); *A61N 2005/1094* (2013.01)

(58) Field of Classification Search
CPC .... A61B 2090/0427; A61B 2090/0445; A61B 2090/0481; A61B 90/02; A61B 90/04
See application file for complete search history.

(56) References Cited

U.S. PATENT DOCUMENTS

| | | | |
|---|---|---|---|
| 2004/0167613 A1* | 8/2004 | Yodfat | A61F 2/01 623/1.15 |
| 2007/0093899 A1* | 4/2007 | Dutoit | A61B 17/686 623/17.11 |
| 2007/0129593 A1* | 6/2007 | Gueye | A61N 5/1027 600/7 |
| 2007/0208366 A1* | 9/2007 | Pellegrino | A61M 29/02 606/198 |
| 2008/0011946 A1* | 1/2008 | Suh | A61N 5/1048 250/252.1 |

(Continued)

*Primary Examiner* — Baisakhi Roy
(74) *Attorney, Agent, or Firm* — Jackson IPG PLLC; Demian K. Jackson

(57) ABSTRACT

The present invention provides a human tissue radiation protector with auxiliary method of radiotherapy, wherein said human tissue radiation protector comprises an interconnected expander, a syringe and a marker set onto the expander; said marker is made of radiopaque materials, which could assist the expander in positioning; as well as multiple radiation dosage detector capable of measurement the radiation dosage at different positions of the expander; said method allows to place the expander of the human tissue radiation protector between the tumor and nearby human tissues or organs so as to separate them, and assist the expander in positioning via the marker and measurement the radiation dosage via the radiation dosage detector.

6 Claims, 5 Drawing Sheets

(56) References Cited

U.S. PATENT DOCUMENTS

| | | | |
|---|---|---|---|
| 2008/0033471 A1* | 2/2008 | Paz | A61B 17/0218 606/190 |
| 2011/0095195 A1* | 4/2011 | Imai | H01L 27/14625 250/370.08 |
| 2011/0130822 A1* | 6/2011 | Cottone | A61F 2/91 623/1.15 |
| 2012/0150190 A1* | 6/2012 | Rabiner | A61B 17/1615 606/100 |
| 2013/0023715 A1* | 1/2013 | Raleigh | A61N 5/1037 600/1 |
| 2014/0018732 A1* | 1/2014 | Bagaoisan | A61M 25/0147 604/95.04 |
| 2014/0018806 A1* | 1/2014 | DiPoto | A61B 17/921 606/63 |

* cited by examiner

HUMAN TISSUE RADIATION PROTECTOR WITH AUXILIARY METHOD OF RADIOTHERAPY

This is a continuation application of Ser. No. 14/249,766 filed on Apr. 10, 2014.

BACKGROUND OF INVENTION

1. Field of the Invention

The present invention relates generally to an auxiliary radiotherapy equipment, and more particularly to an innovative one which is involved with a human tissue radiation protector with auxiliary method of radiotherapy.

2. Description of Related Art

A tissue expander is mainly used for expanding the human tissue, and structurally comprised of an elastic capsular bag (and/or a syringe connected to the capsular bag). According to the operating method of conventional tissue expander, a capsular bag is implanted under the skin of patients, and when necessary, filled with a predefined amount of (depending on the skin status and tolerance of patients) solution (e.g.: physiological saline) or air, so as to expand gradually the skin for skin transplantation or placing specific object under the skin (physiological saline bag or silica for false breast or breast enlargement).

Secondly, as illustrated in US patent publication No. 20080033471 "Device System And Method For Tissue Displacement Or Separation", an airbag unit is implanted surgically into the human body, and then expanded by means of air injection to separate the human tissues or organs for subsequent medical activities. Such airbag unit is made of absorbable materials, so it is not required to be taken out after implantation; yet, it can only separate the human tissues or organs other than accurately locating and detecting their position (special imaging method is required), so it is not suitable for high-accuracy radiotherapy.

When radiotherapy is applied to tumor(cancer cells), some normal cells close to the tumor(cancer cells) will be affected; according to the prevailing practice, the physician in charge of radiotherapy is obliged to control the radiation incidence angle and dosage, but finding it difficult to avoid damage against normal cells.

If the tumor and normal cells could be fully separated, it is possible theoretically to reduce the damage against normal cells when conducting radiotherapy against cancer cells; however, as disclosed in aforementioned US patent, it is difficult to locate securely the airbag unit, leading to poor effect of radiotherapy; also, there lacks of a radiation protector unit that can separate the cancer cells and normal cells for radiotherapy treatment.

SUMMARY OF THE INVENTION

The primary objective of the present invention is to provide a human tissue radiation protector with auxiliary method of radiotherapy, which could not only separate the tumor from the human organs or tissues, mitigate the damage of radiation against nearby tissue, but also locate easily them to improve the accuracy of radiotherapy.

Another objective of the present invention is to provide a human tissue radiation protector with auxiliary radiotherapy, which could measure the dosage of radiation at different positions.

The present invention provides a human tissue radiation protector, which comprising: an expander with a filling space, made of radiolucent materials, which can be implanted into the human tissue to separate the tumor from nearby human tissue or organs; a syringe, linked to the filling space, and used to input the predefined fluid into the filling space for expanding the expander; a marker, made of radiopaque materials, set onto the expander for the positioning of expander.

The present invention also provides an auxiliary method of radiotherapy, whereby the expander of the human tissue radiation protector is arranged between the tumor and nearby human tissue or organs, so as to separate them and assist the expander in positioning via the help of the marker.

Furthermore, the present invention also provides an auxiliary method of radiotherapy, whereby the expander is arranged between the tumor and nearby human tissue or organs, so as to separate them and assist the expander in positioning and also measuring the dosage using radiation dosage detector.

DETAILED DESCRIPTION OF THE INVENTION

Figure 1:
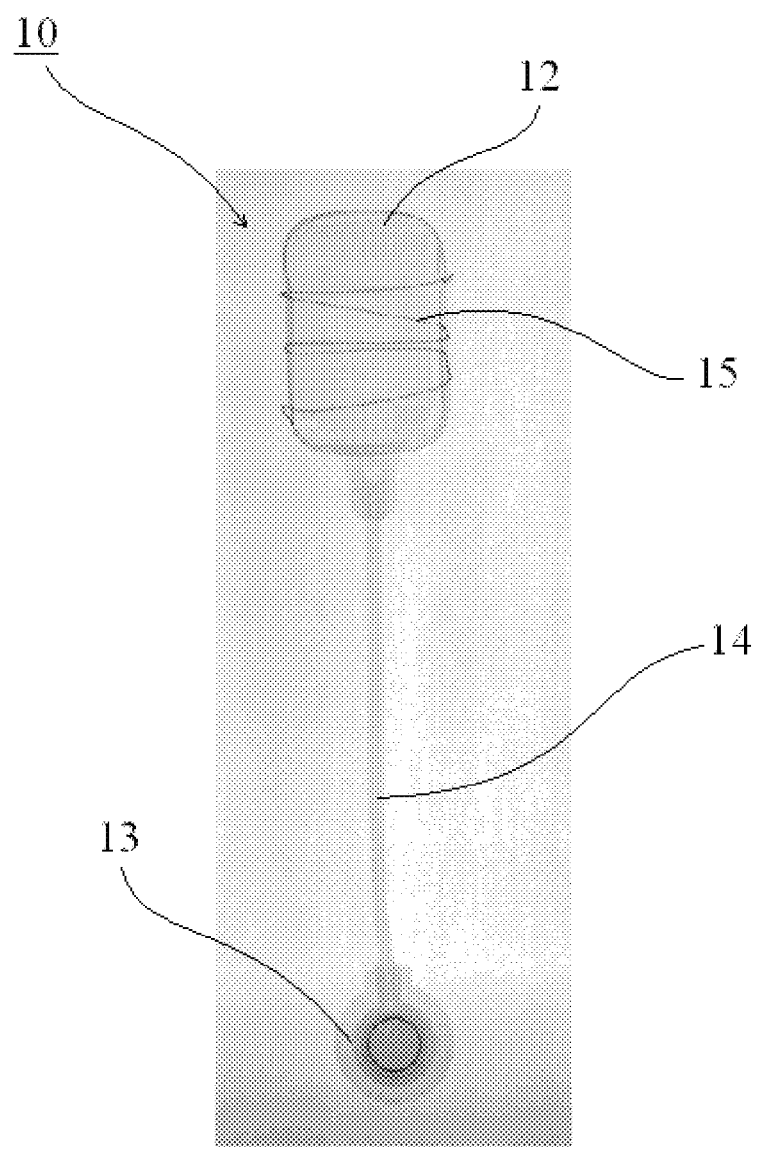
FIG. 1 is a front view of a preferred embodiment of the present invention.
Figure 2:
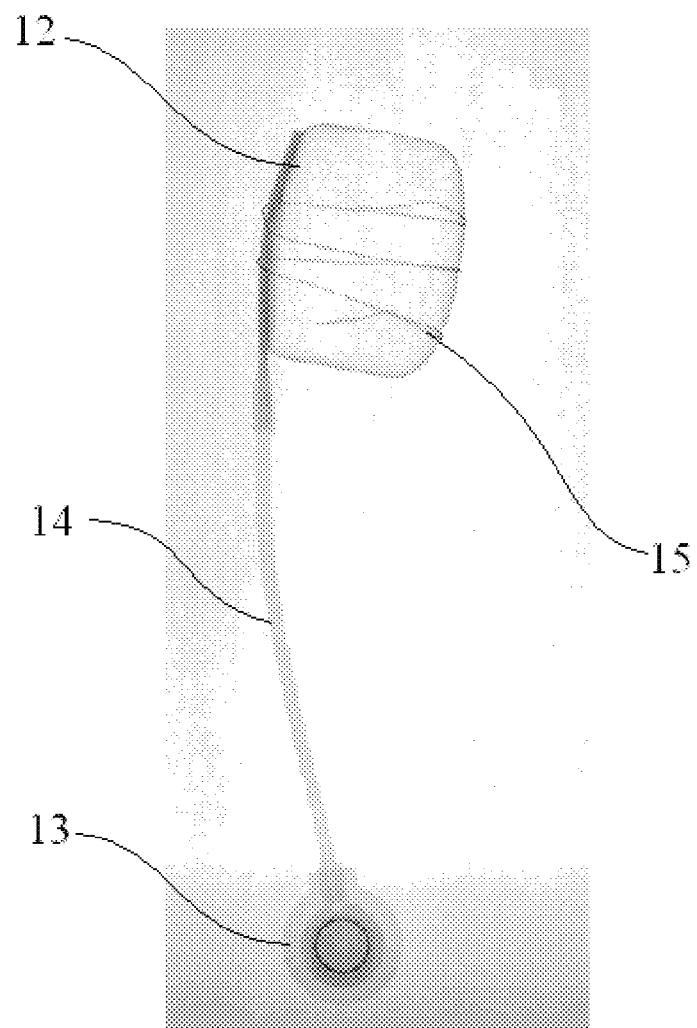
FIG. 2 is a side view of a preferred embodiment of the present invention.
Figure 3A:
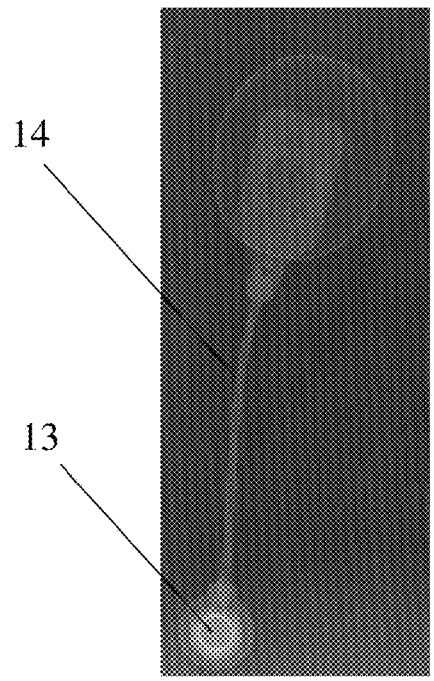
FIG. 3(*a*)-(*c*) is the radiograph of the marker which is a thread or sheet containing a plurality of gold points (golden material).
Figure 3B:
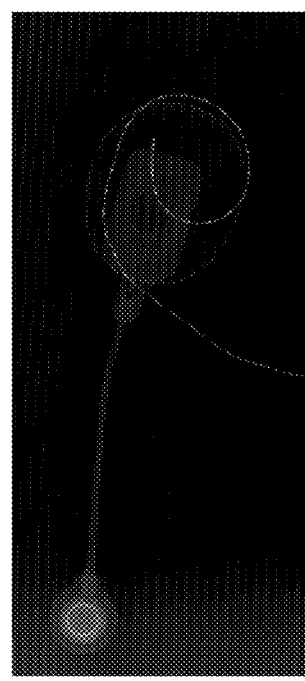
Figure 3C:
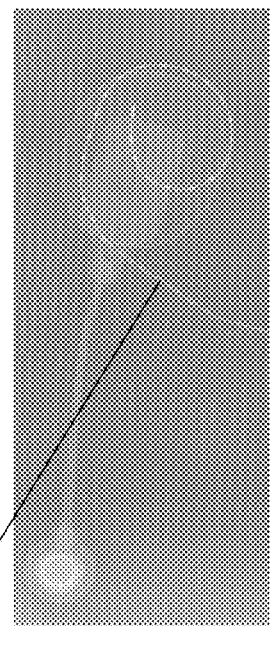

Referring to FIGS. 1 and 2, the human tissue radiation protector 10 in a preferred embodiment of the present invention comprises: an expander 12, a syringe 13 and a tube 14 linked to the expander 12 and syringe 13; said syringe 13 is used to inject fluid (air or solution) to the expander 12; said human tissue radiation protector 10 is characterized by that, it also comprising:

a marker 15, made of radiopaque materials (e.g.: by X-ray), set onto the surface of the expander 12 or directly molded into the expander 12, and used to assist in detecting the position of the expander 12 and localizing it in the human tissue; in the preferred embodiment, a cotton thread is wound onto the surface of the expander 12; the marker 15 is a thread or sheet containing a plurality of gold points (golden material) as shown in FIG. 3, three-dimensional position of the gold points can help to know the distance and three-dimensional spatial coordinates between the tumor and human organs or tissues.

With this design, the operating methods, features and efficacies of the human tissue radiation protector 10 of the present invention are described below:

The human tissue radiation protector 10 is used for radiation therapy in a manner that the expander 12 is implanted between the tumor (cancer cells) and human tissues or organs, then liquid (air or solution) is injected by the syringe 13 so that the expander 12 is expanded to separate the tumor (cancer cells) from the human tissues or organs, enabling the physicians to conduct radiotherapy treatment without damage against the human tissues or organs.

Secondly, as the expander 12 is made of soft materials that cannot be accurately located after being implanted into the human tissues, the marker 15 of the present invention, which is made of radiopaque materials, is used to assist the expander 12 in accurate positioning to realize the effect of fixed scale.

Figure 4:
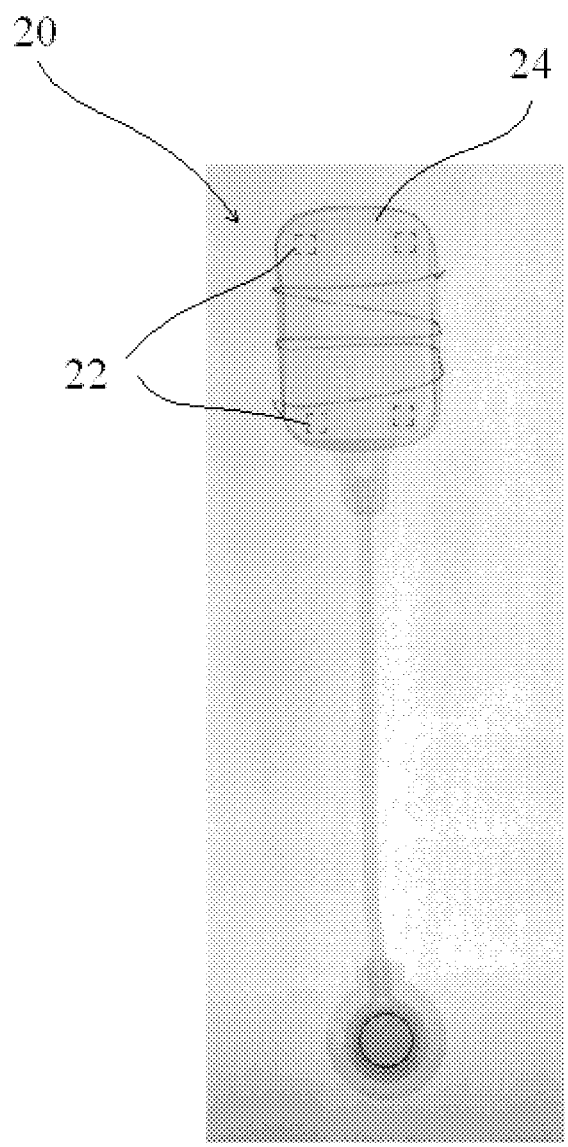
FIG. 4 is a front view of another preferred embodiment of the present invention.

Referring to FIG. 4, the human tissue radiation protector 20 in another preferred embodiment of the present invention has a similar structure compared with the human tissue radiation protector 10; its difference lies in that, multiple radiation dosage detectors 22 are set at different positions within the expander 24 (e.g.: the film or thermoluminescent dosimeter, TLD and chemical dosimeter capable of detecting electromagnetic radiation), so as to measure the radiation dosage at different positions of the expander 24. With this design, the human tissue radiation protector 20 allows to evaluate the radiation dosage by the radiation dosage detectors 22 within the expander 24, thus improving the accuracy of radiotherapy.

With the design of the marker, the human tissue radiation protector of the present invention could not only separate the tumor from the human tissues or organs, mitigate the damage of radiation against nearby tissues, but also locate easily them to improve the accuracy of radiotherapy. Furthermore, with the setting of the radiation dosimeter, it is easier to detect and evaluate the radiation dosage at different positions of the expander, so as to enhance the accuracy of the radiotherapy.

It is thus learnt that, the present invention also provides an auxiliary method of radiotherapy, which allows to arrange the expander of the human tissue radiation protector between the tumor cells and nearby human tissues or organs; then, the syringe is extended out of the human body via the tube, so that the tumor cells are separated from the nearby human tissues or organs, and the marker is used to assist the expander in positioning, or the radiation dosimeter is used to detect the radiation dosage at different positions of the expander.

Figure 5:
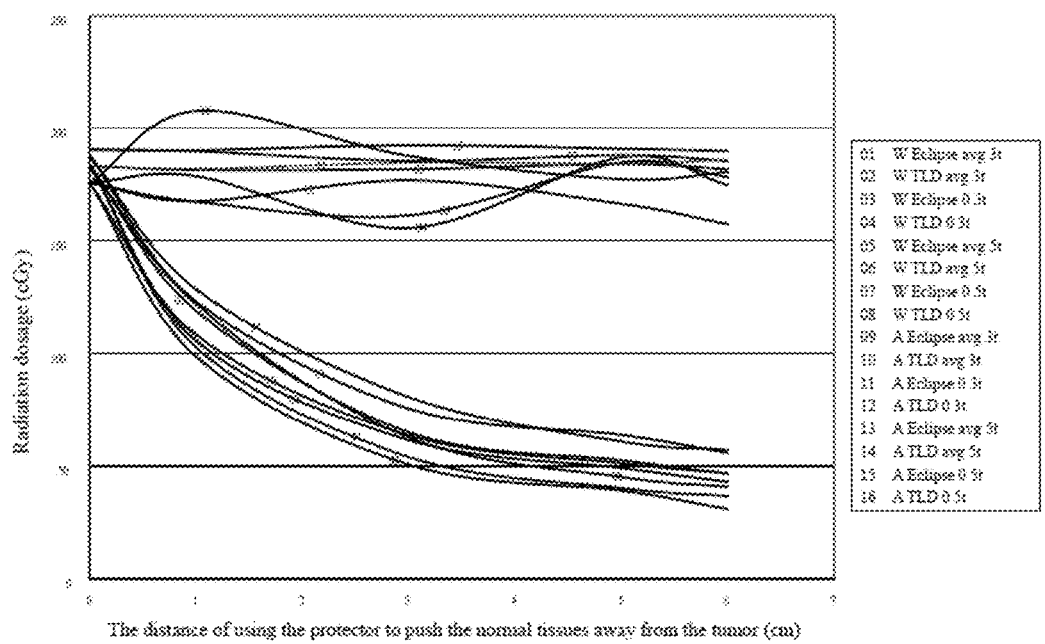
FIG. 5 is a change chart of the radiation dosage of the present invention when normal tissues are separated from the tumor.

The aforementioned efficacies of the human tissue radiation protector of the present invention are validated by means of in-vitro implementation:

In-vitro implementation: air and liquid is separately filled into the expander, the radiation dosage difference is simulated when normal cells near to 3 cm and 5 cm tumor cells are further pushed away 1 cm, 3 cm, 5 cm and 6 cm, separately by a radiation protector; then a clinical treatment planning system is used to calculate the radiation dosage of normal cells, and conduct radiation measurement by taking conventional thermoluminescent dosimeter (TLD) as the radiation dosage detector, with the results shown in FIG. 5, wherein W represents water filled into the expander, and A represents air filled into the expander; when the radiation protector is filled with liquid, and normal cells are pushed 3 cm away from 3 cm tumor cells, the received radiation dosage will be reduced efficiently by 50%; in other words, if normal cells are under the same radiation dosage, a human radiation protector could be used to push away normal cells, so the effect of radiotherapy could be raised by adding 50% radiation dosage to the tumor.

To sum up, with the design of the marker and radiation dosage detector, the present invention could not only separate the tumor from the human organs or tissues, mitigate the damage of radiation against nearby tissues, but also locate easily them to improve the accuracy of radiotherapy. Hence, as present invention not yet publicly available complies with the spirit of new patents, so the patent claims are made hereto.

What is claimed is:

1. A human tissue radiation protector comprising:
an expander with a filling space, made of radiolucent materials, and configured to be implanted into human tissue to separate a tumor from nearby human tissue or organs;
one or more radiation dosage detectors set at one or more corresponding different positions within the expander to measure a radiation dosage at the one or more corresponding different positions of the expander;
a syringe, linked to the filling space, and configured to input a predefined fluid into the filling space for expanding the expander; and
a marker made of radiopaque materials spirally wound around said filling space of the expander to facilitate positioning of the expander; and wherein said marker is a thread containing a plurality of gold points such that a radiograph of the gold points describes a broken line, wherein three-dimensional positions of the gold points define a distance and three-dimensional spatial coordinates between the tumor and human organs or tissues.

2. The structure defined in claim 1, wherein each said one or more radiation dosage detector is film, a thermoluminescent dosimeter (TLD), or chemical dosimeter capable of detecting electromagnetic radiation.

3. An auxiliary method of radiotherapy comprising arranging the expander of the human tissue radiation protector defined in claim 1 between tumor cells and nearby human tissues or organs to separate the tumor cells from the nearby human tissues or organs; and employing the marker and one or more radiation dosage detectors to assist the expander in positioning and measure the radiation dosage at different positions of the expander; thereby, said expander and marker are located inside of the human body.

4. The method of claim 3, wherein said syringe is located inside or outside of the human body.

5. The method of claim 3, wherein each said one or more radiation dosage detector is film, a thermoluminescent dosimeter (TLD), or chemical dosimeter capable of detecting electromagnetic radiation.

6. A method of radiotherapy comprising;
arranging a radiolucent expander comprising:
a filling space;
one or more radiation dosage detectors which are set at one or more corresponding different positions within the expander to measure a radiation dosage at one or more corresponding different positions of the expander;
a syringe, linked to the filling space, and configured to input a predefined fluid into the filling space so as to expand the expander; and
a marker made of radiopaque materials set onto a surface of the expander and containing a plurality of gold points, wherein a radiograph of the gold points describes a broken line and wherein three-dimensional positions of the gold points define a distance and three-dimensional spatial coordinates between a tumor and human organs or tissue;
positioning the syringe inside or outside of a human body between tumor cells and nearby human tissues or organs;
actuating the syringe to expand the expander so as to separate the tumor cells from the nearby human tissues or organs; and employing radiograph imaging of the marker and one or more radiation dosage detectors to position the expander and measuring a radiation dosage at different positions of the expander.

* * * * *